United States Patent
Boua et al.

(10) Patent No.: US 10,675,238 B2
(45) Date of Patent: Jun. 9, 2020

(54) HAIR COMPOSITION

(71) Applicant: Conopco, Inc., Englewood Cliffs, NJ (US)

(72) Inventors: Aikaterini Boua, Wirral (GB); Lalitesh Chandra, Northampton (GB)

(73) Assignee: CONOPCO, INC., Englewood Cliffs, NJ (US)

( * ) Notice: Subject to any disclaimer, the term of this patent is extended or adjusted under 35 U.S.C. 154(b) by 0 days.

(21) Appl. No.: 15/746,204

(22) PCT Filed: Jul. 7, 2016

(86) PCT No.: PCT/EP2016/066124
§ 371 (c)(1),
(2) Date: Jan. 19, 2018

(87) PCT Pub. No.: WO2017/016841
PCT Pub. Date: Feb. 2, 2017

(65) Prior Publication Data
US 2018/0207083 A1     Jul. 26, 2018

(30) Foreign Application Priority Data
Jul. 29, 2015   (EP) .................................... 15178890

(51) Int. Cl.
*A61Q 5/00*      (2006.01)
*A61K 8/891*     (2006.01)
(Continued)

(52) U.S. Cl.
CPC ............... *A61K 8/891* (2013.01); *A61K 8/04* (2013.01); *A61K 8/25* (2013.01); *A61K 8/26* (2013.01); *A61K 8/31* (2013.01); *A61K 8/585* (2013.01); *A61K 8/895* (2013.01); *A61Q 5/065* (2013.01); *A61K 2800/43* (2013.01)

(58) Field of Classification Search
CPC . A61K 8/04; A61K 8/25; A61K 8/891; A61K 8/895; A61K 8/89; A61K 2800/43; A61Q 5/065
See application file for complete search history.

(56) References Cited

U.S. PATENT DOCUMENTS

| 4,987,169 A | 1/1991 | Kuwata |
| 5,654,362 A | 8/1997 | Schulz, Jr. |

(Continued)

FOREIGN PATENT DOCUMENTS

| EP | 2022471 | 2/2009 |
| EP | 2022478 | 2/2009 |

(Continued)

OTHER PUBLICATIONS

IPRP2 in PCTEP2016066124, dated Sep. 22, 2017.
(Continued)

*Primary Examiner* — Eisa B Elhilo
(74) *Attorney, Agent, or Firm* — Foley & Lardner LLP

(57) ABSTRACT

The present invention provides a hair treatment composition comprising; a. 40-99 w.t. % of a dispersion of a loosely reticulated silicone elastomer solvent; b. a compound selected from; i. 0.005-8 w.t % temporary dye ii. 0.005-12 w.t. % semi-permanent dye iii. 0.001-6 w.t. % pigment and mixtures thereof, c. 0.005 w.t. % to 59 w.t. % carrier material.

20 Claims, 2 Drawing Sheets

Figure 1:
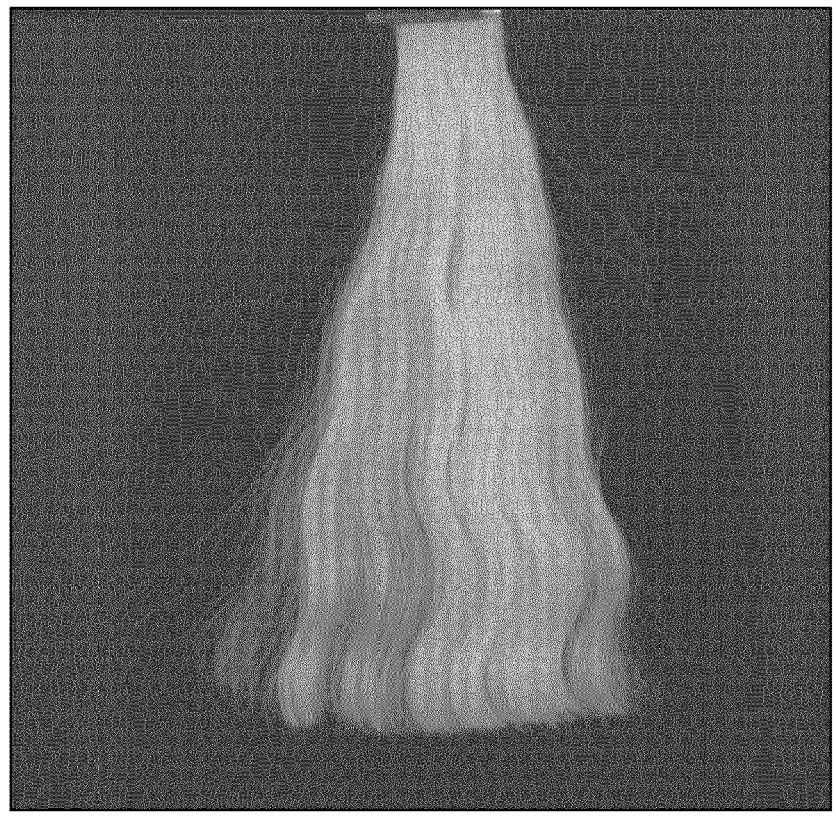

(51) Int. Cl.
*A61K 8/26* (2006.01)
*A61Q 5/06* (2006.01)
*A61K 8/895* (2006.01)
*A61K 8/31* (2006.01)
*A61K 8/58* (2006.01)
*A61K 8/04* (2006.01)
*A61K 8/25* (2006.01)

(56) References Cited

U.S. PATENT DOCUMENTS

| | | | |
|---|---|---|---|
| 8,222,363 | B2 | 7/2012 | Lin et al. |
| 2002/0102225 | A1 | 8/2002 | Hess et al. |
| 2002/0106385 | A1 | 8/2002 | Vatter et al. |
| 2002/0120989 | A1 | 9/2002 | Gomez |
| 2007/0044251 | A1 | 3/2007 | Kravtchenko et al. |
| 2007/0044252 | A1 | 3/2007 | Kravtchenko et al. |
| 2007/0297996 | A1 | 12/2007 | Tanner |
| 2008/0038216 | A1* | 2/2008 | Zukowski ............ A61K 8/8111 424/70.12 |
| 2008/0145443 | A1 | 6/2008 | Langolf et al. |
| 2009/0031505 | A1 | 2/2009 | Kravtchenko et al. |
| 2012/0145177 | A1 | 6/2012 | Thompson et al. |
| 2013/0142748 | A1* | 6/2013 | Tamura ................ A61K 8/894 424/70.12 |
| 2014/0060768 | A1 | 3/2014 | Hasenbusch |
| 2016/0331671 | A1 | 11/2016 | Burns et al. |

FOREIGN PATENT DOCUMENTS

| | | |
|---|---|---|
| FR | 3004343 | 10/2014 |
| GB | 2385056 | 8/2003 |
| JP | 201037202 | 2/2010 |
| WO | WO2007125236 | 11/2007 |
| WO | WO2009033399 | 3/2009 |
| WO | WO2010025897 | 3/2010 |
| WO | WO2010108088 | 9/2010 |
| WO | WO2011082019 | 7/2011 |
| WO | WO2013158844 | 10/2013 |
| WO | WO2013190709 | 12/2013 |
| WO | WO2014167543 | 10/2014 |
| WO | WO2015035164 | 3/2015 |

OTHER PUBLICATIONS

Search Report & Written Opinion in EP15178890, dated Feb. 25, 2016.
Search Report and Written Opinion in PCTEP2016066124, dated Sep. 12, 2016.
Written Opinion 2 in PCTEP2016066124, dated Jun. 27, 2017.

* cited by examiner

HAIR COMPOSITION

FIELD OF THE INVENTION

The present invention relates to a hair composition comprising silicone elastomer and a dye or pigment.

BACKGROUND OF THE INVENTION

Consumers with dyed hair suffer from colour fade, loss of shine and dried out hair, which becomes frizzy and difficult to manage. Other consumers, with undyed hair seek temporary or semi-permanent colour and shine, combined with smooth and easy to manage hair.

Products currently available to consumers are aqueous based creams, providing 'top up' or toning levels of dyes. There however remains a need for improved delivery of dyes and pigments to the hair and improved finish of the hair.

Unpublished application PCT/EP2015/050115 discloses a hair composition comprising silicone elastomer, which can be applied to dry or damp hair to give a smooth, soft finish with light hold and frizz reduction.

The composition of this invention provides a dye and pigment delivery system, providing uniform delivery to hair with the additional benefit of smooth, less frizzy hair.

SUMMARY OF THE INVENTION

Accordingly the present invention provides a hair treatment composition comprising;
- a. 40-99 w.t. % silicone elastomer
- b. a compound selected from;
  - i. 0.005-8 w.t % temporary dye
  - ii. 0.005-12 w.t. % semi-permanent dye
  - iii. 0.001-6 w.t. % pigment
  - and mixtures thereof,
- c. 0.005 w.t. % to 59 w.t. % carrier material

DETAILED DESCRIPTION OF THE INVENTION

The composition of the invention is preferably a soft product, for example a paste. The soft nature of the composition enables better distribution of the product throughout the hair and ensures uniform colour delivery to the hair.

The softness may be defined in terms of parameters G' and G", where G' is the storage modulus which is a measure of the energy stored in a material in which a deformation has been applied and G" is the loss modulus which is a measure of energy dissipated in a material in which a deformation has been applied.

G' and G" follow a log scale.

In the composition of the invention, the storage modulus G' is preferably in the range of from 50 to 2500 cPs, more preferably 100 to 1750, most preferably from 200 to 1000 and the loss modulus G" is preferably in the range of from 50 to 1500 cPs, preferably from 75 to 1000, most preferably from 100 to 500.

Storage and loss moduli may suitably be measured by dynamic mechanical spectroscopy.

Preferably, the compositions of the invention have a viscosity of from 250,000 to 600,000 cPs, preferably from 350,000 to 500,000 cPs, as measured by T-bar, at 0.5 rpm and 25° C.

Silicone Elastomer

The composition of the present invention comprises silicone elastomers.

Silicone elastomers are well known in the art. According to (http://www.dowcorning.com/content/publishedlit/Chapter16.pdf)

"Silicone elastomer dispersions are cross-linked gels that can be prepared through a hydrosilylation reaction. The reaction involves low levels of catalyst, usually platinum derivatives, and is generally run into an adequate solvent. SiH containing silicone polymers are reacted with di-vinylic materials to link independent silicone chains. If the reaction is carried out in cyclic PDMS as the solvent, it leads to the formation of a swollen and loosely-reticulated network or a silicone elastomer dispersion."

The silicone elastomers of use in the present invention and their methods of manufacture are described in U.S. Pat. Nos. 4,987,169, 8,222,363 and 5,654,362.

The silicone elastomers used in the present invention are dispersions of a loosely reticulated silicone in a solvent.

Examples of the solvent include isododecane, isodecyl neopentanoate, cyclopentasiloxane, dimethicone, isohexane, vinyl dimethicone and hydrogen dimethicone.

Examples of silicones which may be dispersed in a solvent to form an elastomer include:

- Dimethicone/Bis-Isobutyl PPG-20 Crosspolymer, Dimethicone Crosspolymer, Dimethicone, vinyl dimethicone, hydrogen dimethicone, 2,4,6,8-tetravinyl cyclotetrasiloxane
- Isododecane (and) Dimethicone/Bis-Isobutyl PPG-20 Crosspolymer commercially available from Dow Corning as Silicone Elastomer EL-8051;
- Isodecyl Neopentanoate (and) Dimethicone/Bis-Isobutyl PPG-20 Crosspolymer commercially available from Dow Corning as Silicone Elastomer EL-8052;
- Isohexadecane (and) Dimethicone/Bis-Isobutyl PPG 20 Crosspolymer commercially available from Dow Corning as Silicone Elastomer 9040;
- Cyclopentasiloxane (and) Dimethicone Crosspolymer commercially available from Dow Corning as Silicone Elastomer 9041;
- Dimethicone (and) Dimethicone Crosspolymer commercially available from Dow Corning as Silicone Elastomer 9045; and
- Dimethicone, vinyl dimethicone, hydrogen dimethicone, 2,4,6,8-tetravinyl cyclotetrasiloxane.

The silicone elastomer (dispersed silicone in solvent) is present in the compositions of the invention at from 40 to 99 w.t. % of the composition, preferably, at from 40 to 95 w.t. %, more preferably at from 42 to 85 w.t. %, most preferably 51 to 85 w.t. % of the composition.

Dye or Pigment

The composition of the present invention comprises a compound selected from temporary dyes, semi-permanent dyes, pigments and mixtures thereof.

In one preferred embodiment the composition comprises a temporary or semi-permanent dye and a pigment. The composition may comprise;
- i. a dye selected form 0.005-12 w.t. % temporary dye or 0.005-12 w.t. % semi-permanent dye; and
- ii. 0.001-6 w.t. % pigment.

Temporary and Semi-Permanent Dyes

Dyes suitable for the present invention are either temporary or semi-permanent dyes. Temporary or semi-permanent dyes are not oxidation dyes and do not require a developer.

Semi-permanent dyes penetrate the hair shaft. They can also be referred to as direct dyes. Preferred semi-permanent hair dyes are nitro or azo dyes. The composition may comprise 0.005-12 w.t. % semi-permanent dye, preferably 0.01-6 w.t. % semi-permanent dye, more preferably 0.01-2 w.t. % semi-permanent dye, most preferably 0.01-1 w.t. % semi-permanent dye.

Temporary dyes adsorb on to the hair shaft. Temporary dyes may be water or oil soluble. They may be acid or basic. Generally have a high molecular weight. The composition may comprise 0.005-8 w.t % temporary dye, preferably 0.01-4 w.t. % temporary dye, more preferably 0.01-2 w.t. % temporary dye, most preferably 0.01-1 w.t. % temporary dye.

The dyes may be any colour desired by a consumer. The colours may be for a natural look such as black, brunette, blonde or violet to tone naturally blonde hair or bleach blonde hair or the colours may be for an un-natural look such as blue, green or purple.

Pigment

Pigment materials are materials which change the colour reflected if transmitted from a surface. Pigments suitable for the present invention include inorganic, metallic and organic/biological pigments. Preferably the pigment is an inorganic or metallic pigment. Most preferably the pigment is a mica pigment.

Mica pigments are obtained by applying a thin coating of titanium dioxide, optionally with tin oxide and/or possible silicon dioxide to the surface of the mica, which often have adopted the physical form of platelets. In some instances, the coating further incorporates a minor fraction of a transition metal oxide, including in particular iron, chromium, copper or cobalt oxides or a combination of two or more of them. By incorporating the metal oxide, the resultant material exhibits a colour highlight that supplements the reflective character of the substrate mica. Such pigments are commonly called interference pigments. It is particularly preferred to select an interference pigment that exhibits a highlight having a wavelength of below 550 nm, particularly below 500 nm. Many preferred pigments exhibit a highlight of wavelength greater than 400 nm and particularly from 450 nm. In other words, interference pigments having a violet or indigo tint are preferred and those having a blueish tint are much preferred. Suitable and/or preferred mica pigments including mica interference pigments are commercially available, such as various grades from Merck Inc under their trade mark Timiron.

The composition may comprise 0.001-6 w.t. % pigment, more preferably 0.005-2 w.t. % pigment, most preferably 0.01-0.1 w.t. % pigment.

Preferably the composition comprises 0.001-6 w.t. % mica pigment, more preferably 0.005-2 w.t. % mica pigment, most preferably 0.01-0.1 w.t. % mica pigment.

Carrier Material

The composition of the present invention comprises a carrier material for the dye and/or pigments. The dye and/or pigments require a carrier material to be incorporated into the composition. A carrier material may also be referred to as binder, vehicle, solvent, etc. The carrier material may be polar or non-polar. A suitable carrier material should be selected for the chosen dye and/or pigment, different dyes and pigment may require different carrier materials. If the composition comprises more than one dye or pigment, more than one carrier materials may also be used.

In the compositions of the invention, the dye cannot be present on its own; it needs a carrier. The amount of carrier depends on not only the amount of dye, but also the type of dye. This is because the solubility of the dye affects the amount of carrier required. Further, if another ingredient in the final formulation contains, e.g. an oil, such as for example, a perfume oil, then the amount of additional carrier is reduced to the extent that the dye is oil soluble.

The solvent in the silicone elastomer cannot be a carrier because it is swollen and absorbed within the elastomer. Thus, the carrier defined herein does not include the solvent from the silicone elastomer.

Examples of suitable carrier materials include; oils, silicones, water and emulsifier combinations, hydrocarbons, triglycerides, esters, fatty alcohols, waxes, mineral oils, aromatic hydrocarbons, paraffins, urea, acids, aqueous metal oxide suspensions, organic solvents, inorganic solvents.

In a preferred embodiment the carrier material is selected from; oils, silicones, hydrocarbons and mineral oil, more preferably the carrier material comprises silicones, most preferably volatile silicones.

The composition comprises 0.005 w.t. % to 59 w.t. % carrier material. The amount of carrier material required will be relative to the amount of dye and pigments contained in the composition. Preferably the composition comprises 0.01 w.t. % to 40 w.t. % carrier material, most preferably 0.1 to 10 w.t. % carrier material.

The carrier material may comprise water, the composition may comprise from 0 to 10 w.t. % water, more preferably from 0 to 5 w.t. % water and most preferably from 0 to 0.1 w.t. % water. Optionally the composition may comprise from 0.000001 to 10 w.t. % water, more preferably from 0.000001 to 5 w.t. % water and most preferably from 0.000001 to 0.1 w.t. % water.

Water Content

The composition of the present invention is preferably substantially water free. The composition may comprises from 0 to 10 w.t. % water, more preferably from 0 to 5 w.t. % water and most preferably from 0 to 0.1 w.t. % water. This includes any water contained in the carrier material.

Optionally the composition may comprise from 0.000001 to 10 w.t. % water, more preferably from 0.000001 to 5 w.t. % water and most preferably from 0.000001 to 0.1 w.t. % water.

Silica

The composition of the invention may optionally also comprises silica. Preferably, the silica is fumed silica.

More preferably, the silica is suspended in oil when added to the composition of the invention. The oil facilitates suspension of the silica within the composition. Where the silica is fumed silica it is preferred that the oil is a light mineral oil or fragrance oil. Preferably, the light mineral oil has a density of from 0.7 to 0.85 g/ml. Density of the mineral oil is also known as specific gravity and is measured according to ASTM D 4052 at 15.6 C.

Preferably, the silica is present at from 0.01 to 5% w.t. of the composition, more preferably from 0.05 to 2% wt.

Volatile Silicone

Preferably, the composition of the invention additionally comprises volatile silicone. The volatile silicone is in addition to any volatile silicone comprised in the silicone elastomer, dye carrier material or silica component. Suitable volatile silicones are well known in the art and include DC245 commercially available from Dow Corning. The volatile silicone may be a mix of volatile silicones.

Preferably, when present, the volatile silicone is present at from 0.1 to 30% wt. of the composition and more preferably from 1 to 5% wt.

Other Optional Components

The composition may preferably comprise a styling aid. Preferred styling aids include silicone resins. A particularly preferred silicone resin is known as an MQ resin. MQ resins are a condensation product between monofunctional silane (M) and tetrafunctional silane (Q). Preferred MNQ resins are available commercially from Dow Corning and include MQ resin CF-0410.

The MQ resin is present at from 0.1 to 5% wt. of the composition and preferably at from 2 to 4% wt.

Preferably, the composition may also comprises an oil selected from mineral oil, vegetable oil and animal oil. Preferably the oil is a mineral oil, most preferably a mineral oil with a density of 0.81 to 0.89 g/cm$^3$ at 20° C. Preferably, such oil is present at from 0.1 to 30 w.t. % of the composition and more preferably from 3 to 10 w.t. %.

Preferably the composition also comprises a perfume or fragrance.

The composition of the present invention may comprise other components suitable for hair care compositions, for example; viscosity modifiers, solvents, preservatives, fragrances, colorants (in addition to the hair dye), pH adjusters, emollients, conditioning agents.

EXAMPLES

TABLE 1

Comparative example A, hair cream composition

| Ingredient | % w.t. |
| --- | --- |
| Violet dye | 0.07 |
| Cetearyl Alcohol | 2.5 |
| Mineral Oil 70 | 3 |
| Stearamidopropyl dimethylamine | 0.7 |
| Cetearyl Alcohol | 2.5 |
| Glycerin | 2 |
| Dimethacone | 1.67 (60% active) |
| Styling polymer | 0.5 (50% active) |
| Minors (inc. fragrance) | 1.25 |
| Water | To 100 |

TABLE 2

Inventive example 1, hair serum composition

| Ingredient | % w.t. |
| --- | --- |
| Dimethicone + Dimethicone Crosspolymer | 83.23 |
| Violet dye | 0.07 |
| Mineral Oil 40 | 7.5 |
| Triglyceride | 5 |
| Volatile silicones | 3 |
| Silica Silylate | 0.5 |
| Fragrance | 0.7 |

Mica was not used in the example compositions because it is believed that it may interfere with the visual analysis.

The two example compositions were used to treat bleached hair switches. The violet dye should tone the bleached blond hair.

Figure 2:
Figure 3:
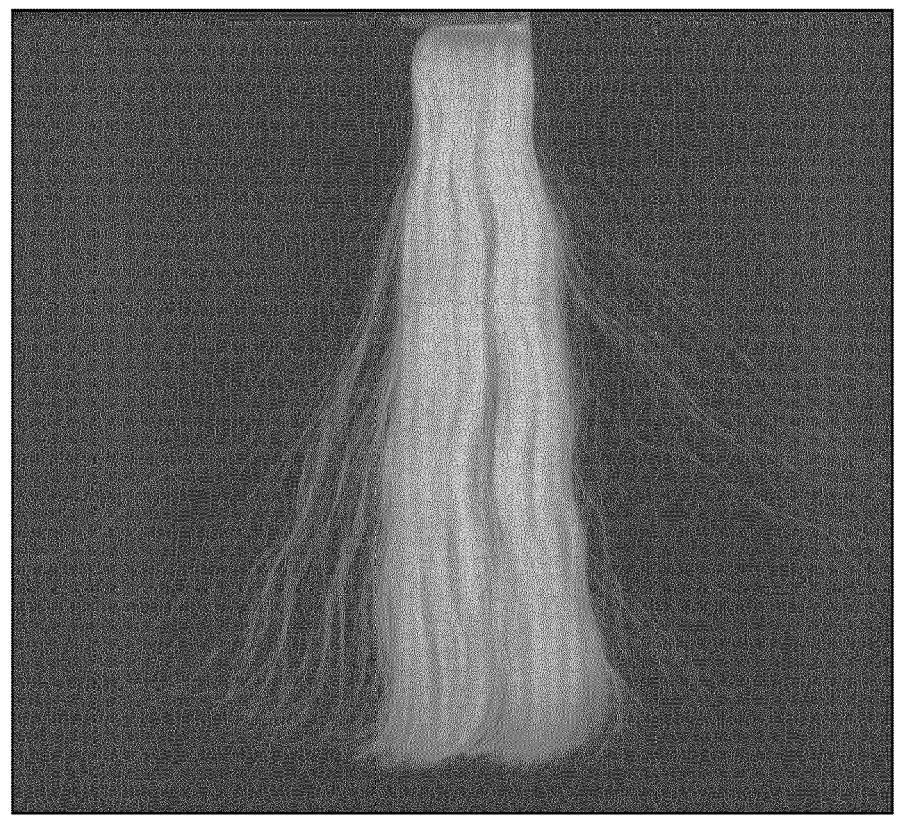
Figure 4:
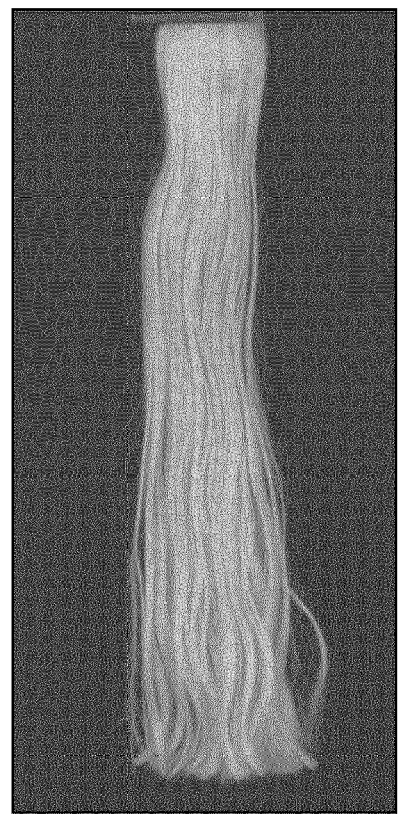

Method
- A photo of the switch was taken before treatment (FIGS. 1 & 2)
- 1 g of hair composition was applied per gram of hair, the composition was applied to the full length of the switch
- The composition was massaged into the hair switch for 1 minute
- The switch was combed 60 times and left to dry overnight at 20° C.
- A photo of the switch was taken the next day (FIGS. 3 & 4)

FIG. 1: Bleached hair switch before being treated with Example A

FIG. 2: Bleached hair switch after being treated with Example A

FIG. 3: Bleached hair switch before being treated with Example 1

FIG. 4: Bleached hair switch before being treated with Example 1

Comparing FIG. 2 and FIG. 4, there is an obvious difference in colour distribution. FIG. 2 has dark marks where the dye has collected and lighter patches where the switch has received no dye. These lighter patches are the light grey colour of untoned, bleached hair. FIG. 4 has an even spread and a warmer, yellower tone, the whole length of the switch.

It can also be seen when comparing FIG. 2 and FIG. 4, that the switch of FIG. 4 is significantly smoother and less frizzy, reflecting the additional benefit of the claimed product.

The invention claimed is:

1. A hair treatment composition comprising;
    a) 40-99 w.t. % of a dispersion of a loosely reticulated silicone elastomer in a solvent;
    b) a composition comprising:
        i. a dye selected from 0.005-8 w.t. % temporary dye or 0.005-12 w.t. % semi-permanent dye; and
        ii. 0.001-6 w.t. % pigment;
    c) 0.005 w.t. % to 59 w.t. % carrier material; and
    d) 0.01 w.t.% to 5 w.t. % of silica.

2. The composition according to claim 1, wherein the pigment is mica.

3. The composition according to claim 1, wherein composition (b) comprises:
    i. 0.01-4 w.t. % temporary dye or
    ii. 0.01-6 w.t. % semi-permanent dye and
    iii. 0.001-6 w.t. % mica.

4. The composition according to claim 1, wherein the carrier material is a silicone.

5. The composition according to claim 1, wherein the composition comprises 0.01 w.t. % to 40 w.t. % carrier material.

6. The composition according to claim 1, wherein the dispersion of the silicone elastomer in the solvent comprises isododecane and dimethicone/bis-isobutyl PPG-20 crosspolymer, isodecyl neopentanoate and dimethicone/bis-isobutyl PPG-20 crosspolymer, isohexadecane and dimethicone/bis-isobutyl PPG-20 crosspolymer, cyclopentasiloxane and dimethicone crosspolymer, or dimethicone and dimethicone crosspolymer.

7. The composition according to claim 1, wherein the composition has a viscosity of from 250,000 to 600,000 cPs, as measured by T-bar, at 0.5 rpm and 25° C.

8. The composition according to claim 1, wherein the carrier material is selected from the group consisting of oils, silicones, water and emulsifier combinations, hydrocarbons, triglycerides, esters, fatty alcohols, waxes, mineral oils, aromatic hydrocarbons, paraffins, urea, acids, aqueous metal oxide suspensions, organic solvents, and inorganic solvents.

9. The composition according to claim 1, further comprising 0.1 w.t.% to 30 w.t.% of volatile silicone.

10. The composition according to claim 1, wherein the pigment is mica comprising a coating of titanium dioxide on a surface of the mica, and wherein the pigment exhibits a highlight having a wavelength below 550 nm.

11. The composition according to claim 1, wherein the composition comprises from 42 w.t.% to 85 w.t.% of the dispersion of the silicone elastomer in the solvent.

12. The composition according to claim 1, wherein the composition comprises from 51 w.t.% to 85 w.t.% of the dispersion of the silicone elastomer in the solvent.

13. The composition according to claim 1, further comprising 0.1 w.t.% to 30 w.t.% of mineral oil having a density of 0.81 to 0.89 g/cm$^3$ at 20° C.

14. The composition according to claim 1, wherein the composition is substantially free of water.

15. A hair treatment composition comprising:
a) 40 w.t.% to 99 w.t. % of a dispersion of a loosely reticulated silicone elastomer in a solvent;
b) a composition comprising:
   i. a dye selected from 0.005 w.t.% to 8 w.t. % temporary dye or 0.005 w.t.% to 12 w.t. % semi-permanent dye; and
   ii. 0.001 w.t.% to 6 w.t. % pigment;
c) 0.005 w.t.% to 59 w.t. % carrier material;
d) 0.01 w.t.% to 5 w.t. % of silica;
e) 0.1 to 30 w.t.% of volatile silicone; and
f) 0.1 w.t.% to 30 w.t.% of mineral oil having a density of 0.81 to 0.89 g/cm$^3$ at 20° C.

16. The composition according to claim 15, wherein the composition comprises 51 w.t.% to 85 w.t.% of the dispersion of the loosely reticulated silicone elastomer in a solvent and 0.1 w.t.% to 10 w.t.% carrier material.

17. The composition according to claim 15, wherein the dispersion of the silicone elastomer in the solvent comprises isodecyl neopentanoate and dimethicone/bis-isobutyl PPG-20 crosspolymer, isododecane and dimethicone/bis-isobutyl PPG-20 crosspolymer, isohexadecane and dimethicone/bis-isobutyl PPG-20 crosspolymer, cyclopentasiloxane and dimethicone crosspolymer, or dimethicone and dimethicone crosspolymer.

18. The composition according to claim 15, wherein the carrier material is selected from the group consisting of oils, water and emulsifier combinations, hydrocarbons, triglycerides, esters, fatty alcohols, waxes, aromatic hydrocarbons, paraffins, urea, acids, aqueous metal oxide suspensions, organic solvents, and inorganic solvents.

19. The composition according to claim 1, wherein the silica is fumed silica.

20. The composition according to claim 15, wherein the silica is fumed silica.

* * * * *